United States Patent [19]
Alt et al.

[11] Patent Number: 5,529,579
[45] Date of Patent: Jun. 25, 1996

[54] IMPLANTABLE AUTOMATIC DIFIBRILLATOR WITH LOW THRESHOLD

[75] Inventors: Eckhard Alt, Ottobrunn, Germany; Lawrence J. Stotts, Lake Jackson, Tex.

[73] Assignee: Intermedics, Inc., Angleton, Tex.

[21] Appl. No.: 242,742

[22] Filed: May 12, 1994

[51] Int. Cl.$^6$ .................................................. A61N 1/375
[52] U.S. Cl. .................................................. 607/36
[58] Field of Search ............................ 607/5, 36, 37

[56] References Cited

U.S. PATENT DOCUMENTS 5,314,430   5/1994   Bardy .......................................... 607/5

*Primary Examiner*—William E. Kamm
*Assistant Examiner*—Scott M. Getzow
*Attorney, Agent, or Firm*—Wigman, Cohen, Leitner & Myers

[57] ABSTRACT

An automatic defibrillator is arranged and adapted to be implanted in a cardiac patient. The defibrillator includes a stimulus generator for sensing fibrillation of the patient's heart and for responding by delivering defibrillation energy to the patient's heart via a defibrillation electrode positioned in the right ventricle of the heart. An electrically conductive case houses the stimulus generator, and a conforming biocompatible electrically non-conductive layer is coated over only a predetermined portion less than all of the case to produce a predetermined shape of electric field between the intracardiac defibrillation electrode and the case when the case is used as an electrode for defibrillation. The predetermined portion of the case coated with the non-conductive layer includes a side of the case to be implanted in a direction facing the heart of the patient, with the non-conductive layer being confined solely to the central portion of that side.

21 Claims, 2 Drawing Sheets

IMPLANTABLE AUTOMATIC DIFIBRILLATOR WITH LOW THRESHOLD

BACKGROUND OF THE INVENTION

The present invention relates generally to medical interventional devices adapted to be implanted in a patient's body, and more particularly to an improved implantable automatic defibrillator having a reduced energy threshold and which may include provision for other cardiac stimulus therapies including cardioversion and antitachycardia, bradycardia and rate-adaptive pacing for the implant patient.

According to the published literature, the first human implant of a completely implantable cardiac defibrillator took place in 1980. Since that time, considerable research has been conducted to provide improvements in such implantable medical devices, focusing on greater efficiency and smaller size. The principal constraints on size reduction have been and remain the batteries and the capacitors required to develop sufficient energy for defibrillating the patient's heart. To date, the large size of these components has dictated bulky and unwieldy stimulus generators, defying until recently any cosmetically acceptable pectoral implantation.

The minimum energy required for defibrillation of either atrium or ventricle constitutes the threshold of the device, which establishes a lower limit on its size. The nature of the delivery system consisting of the specific leads and electrodes and the electrode placement within or on the heart for application of the energy waveform, or shock, generated by the device contribute significantly to the threshold level. Given that the constraints on device size attributable to batteries and capacitors are a function of the technologies relating to those components, improvements in those areas have been left to the physicists and materials engineers. That effort is directed toward attaining long lifetime components with high energy storage capacity.

A parallel effort by cardiologists and biomedical engineers has been concentrated on improving the efficiency of the delivery system. The more efficient the delivery system in applying the shock energy developed by the stimulus generator to excite myocardial tissue for successful defibrillation with minimal energy loss—that is, the lower the threshold—the less energy required to be available from the batteries and capacitors, and consequently the smaller their size within the limits of the component technology. A lower threshold with attendant reduction of shock strength may provide additional benefits to the patient in the form of fewer physiologic side effects such as conduction disturbances, ventricular dysfunction and myocardial necrosis attributable to high energy defibrillation shocks.

The primary effort toward threshold reduction and consequent device size reduction has focused on lead/electrode systems, defibrillation waveforms, and energy vectors for shock delivery. From an original stimulus generator size/weight of approximately 240 grams (g), the state of the art in implantable defibrillators has progressed to a current size/weight of about 130 g.

Various efforts have been made in the past to improve the efficiency of energy delivery by means including use of the housing as a part of the lead/electrode system of the device.

In U.S. Pat. No. 5,133,353, an implantable cardiac stimulation lead system is proposed for pacing, cardioversion and defibrillation functions, in which the lead system includes a transvenous myocardial or pericardial lead having a plurality of electrodes, and the housing of the pulse generator is conductive and connected to the pulse generator circuitry so that it may serve as a discharge electrode. One side wall is a conductive mesh or has a conductive mesh fastened thereto. Such a configuration does not appear to provide any substantial benefits.

It is a principal object of the present invention to provide further reductions in energy threshold of implantable defibrillators, both atrial and ventricular, that would permit substantial size reduction in the stimulus generator, to lessen the onerous side effects on patient physiology and to afford greater cosmetic appeal for implantation in the pectoral region.

Another aim of the invention is to provide an implantable cardioverter/defibrillator in which the housing is used as a shocking electrode for defibrillation, in a manner significantly different from prior usage.

Yet another object is to provide a technique for delivering energy for defibrillating the heart in a way that enables selective concentration of the field to achieve low defibrillation thresholds.

SUMMARY OF THE INVENTION

Briefly, the present invention is directed toward an implantable automatic defibrillator with substantially lowered energy threshold and greater efficiency in energy delivery that allows considerable reduction in the size of the stimulus generator of the defibrillator device. This result is attained owing in principal part to the reduced requirement for energy from the batteries and for energy storage by the associated output capacitors of the device. To that end, according to an aspect of the invention the metal case (sometimes referred to herein as the "can", "enclosure" or "housing") of the stimulus generator of the defibrillator (which, as noted above, may provide for several other types of therapy for the cardiac dysrhythmia patient) is utilized in a shaped or zoned conductive pattern as the electrical ground reference for the device.

Importantly, and in contrast to the prior art, a portion of the exterior surface of the metal case is coated with an electrically non-conductive material, preferably leaving at least a full edge of one side of the case uncoated. When the other electrodes are implanted in the appropriate locations and the defibrillator is activated to deliver the shock energy to the patient's heart, this configuration, which provides special zones of conductivity and nonconductivity on the case, results in the generation of higher field strength toward the outer boundary of the case. The coating material may be parylene or other biocompatible electrically non-conductive material that may be applied with adequate adhesion to the surface of the case. The increased field strength along the uncoated outer boundary of the defibrillator case has been found to greatly diminish the defibrillation threshold (DFT).

Additionally, coating of the back (opposite) side of the stimulus generator case (i.e. the side positioned toward or adjacent the skin of the patient, or, in a retropectoral position, towards the pectoral muscle) serves to avoid energy losses or undesirable stimulation of the pectoral muscle of the patient.

In essence, the invention provides a small implantable cardioverter and defibrillator device adapted for left-sided pectoral implantation in a patient, which includes a shock generator for developing low energy electrical shocks suitable for cardioversion and defibrillation of the patient's heart, an electrical lead having a right ventricular electrode for sensing intracardiac electrical activity, and having a right ventricular shocking coil located on the same lead, and a conductive housing for the shock generator connected as a shocking electrode of the device. The conductivity of the housing is selectively exposed and blocked in a predetermined pattern of zones of electrical conductivity and nonconductivity, which enables the right ventricular shocking coil in conjunction with the housing shocking electrode to enhance the electrical energy field transmission of the device for low energy defibrillation of the patient's heart along the zones of electrical conductivity.

A method of defibrillating a human heart with low energy electrical shocks delivered between the pair of shocking electrodes includes the steps of introducing a right ventricular electrode on a lead into the heart for sensing intracardiac electrical activity, introducing a right ventricular shocking coil located on the same lead as one of the shocking electrodes, implanting a shock generator having a housing with preestablished zones of electrical conductivity and nonconductivity on an external portion of the housing as the other shocking electrode, and delivering the low energy electrical shocks between the right ventricular shocking coil and the housing to develop an electrical field that follows the zones of electrical conductivity on the housing for low energy defibrillation of the patient's heart.

Therefore, another object of the invention is to provide an implantable defibrillator in which the energy field produced by delivery of electrical shock waveforms to the shocking electrodes is concentrated in a zone about the boundary of the case, to lower the DFT.

Still another aim is to use the defibrillator housing with a preestablished zone of conductivity less than all of the housing or than even all of one side of the housing as one shocking electrode in conjunction with a second shocking electrode positioned in the heart.

Although the shocking electrode positioned in the heart is described as being positioned in the right ventricle, the principles of the invention are applicable to atrial defibrillation as well. Accordingly, the latter electrode may be positioned in the right atrium and operate in conjunction with the defibrillator housing that acts as a patterned shocking electrode.

BRIEF DESCRIPTION OF THE DRAWINGS

The above and still further objects, features and attendant advantages of the present invention will become apparent to those skilled in the cardiac stimulation device field from a consideration of the ensuing description of a presently contemplated best mode of practicing the invention as implemented in a preferred embodiment and method, taken in conjunction with the accompanying drawings in which.

DETAILED DESCRIPTION OF THE PREFERRED EMBODIMENT AND METHOD

Figure 1:
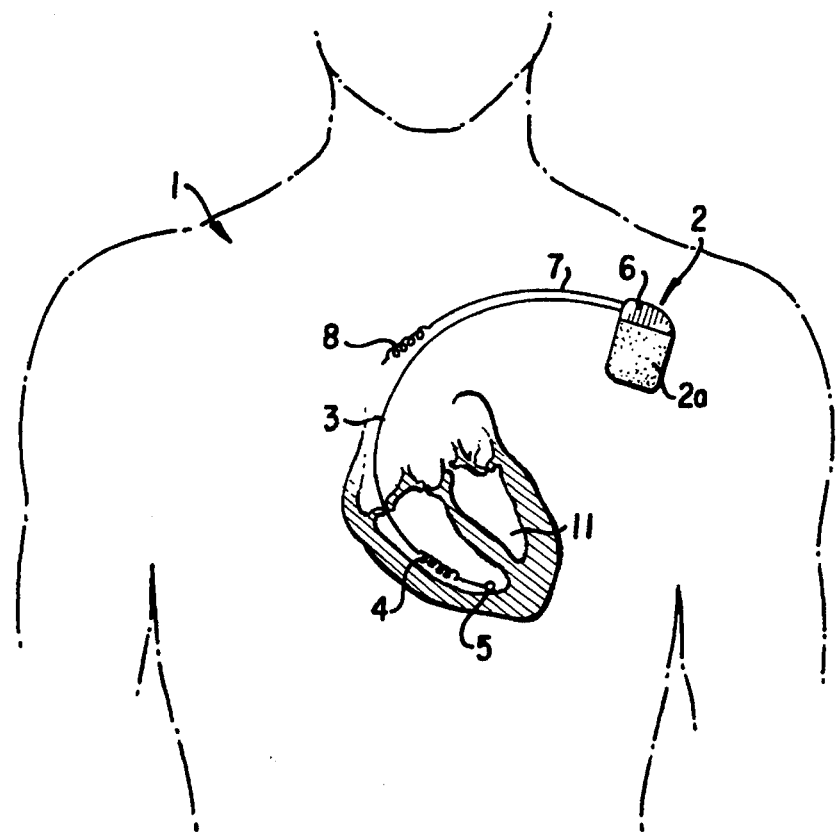
FIG. 1 is a partial front view of a cardiac patient (shown in phantom) in which the improved defibrillator device is implanted, illustrating the location of the major parts of the device including the stimulus generator, leads and electrodes.

Referring now to FIG. 1, a cardiac patient 1 is selected for treatment of the type provided by the present invention by virtue of having had one or more prior episodes of fibrillation or a propensity toward tachycardia which may accelerate into fibrillation. An automatic defibrillator 2 is implanted in the patient by the surgeon using a conventional technique. The defibrillator device includes a stimulus generator 2a which is implanted in a pectoral location, preferably on the patient's left side behind the pectoral muscle to provide the most desirable electrical energy field when the device is operating to perform the defibrillating function. The pectoral location is made possible by the relatively small size of the stimulus generator implemented according to the present invention, as compared to defibrillator stimulus generators in common use.

Stimulus generator 2a is connected to a previously implanted transvenous lead 3 having a defibrillation coil 4 located at or near the distal end so as to be positioned in the right ventricle of the patient's heart. The connection to the proximal end of lead 3 is made by means of a receptacle a standard electrical connector 6 of a header mounted on the stimulus generator case. Lead 3 also has an electrode 5 at its distal tip for use in sensing the cardiac electrical activity and pacing, cardioverting or defibrillating the heart accordingly. Electrode 5 is positioned adjacent the apex of the right ventricle when the lead is fully implanted.

In that regard, the stimulus generator is preferably implemented to provide several distinct cardiac therapies. These include bradycardia and antitachycardia pacing by means of appropriately timed electrical stimulating pulses including single and multiple pulses and pulse trains delivered via the pacing tip electrode 5. Cardioversion is achieved by means of relatively low energy electrical shocks, and defibrillation by means of higher energy level shocks delivered via the defibrillation coil 4.

According to the present-day conventional technology, a second transvenous lead 7 is implanted such that its defibrillation coil 8 at or near the distal end of the lead is disposed transvenously in a location at the vena anonyma or in the superior vena cava, outside the patient's heart. Lead 7 is electrically connected at its proximal end to defibrillator stimulus generator 2a by means of another receptacle of connector 6.

In operation of defibrillator 2 following detection of ventricular fibrillation of the patient's heart, one or more capacitors (not shown) in stimulus generator 2a are rapidly charged to a level for delivery of a shock waveform of sufficient energy applied between coil 4 and coil 8 to defibrillate the ventricles. Typically, the shock is not delivered until ventricular fibrillation is confirmed. Because coil electrode 4 is located in the right ventricle, the majority of the current and voltage in the electric field produced by the shock waveform passes through the mass of the patient's right ventricle 10.

In contrast, such coil positioning produces relatively lower levels of voltage and current through the mass of the left ventricle 11. For effective defibrillation of the left ventricle, then, it is necessary to generate a relatively higher energy field between coil 4 and coil 8 as a consequence of the substantial voltage drop at the outer boundary of the electric field. If coil 8 were instead inserted to be positioned in a location closer to left subclavian vein in an attempt to enhance the electric field through the left ventricle 11, the presence of the patient's lung in the defibrillation field would considerably increase the impedance and further diminish the field strength.

Figure 2:
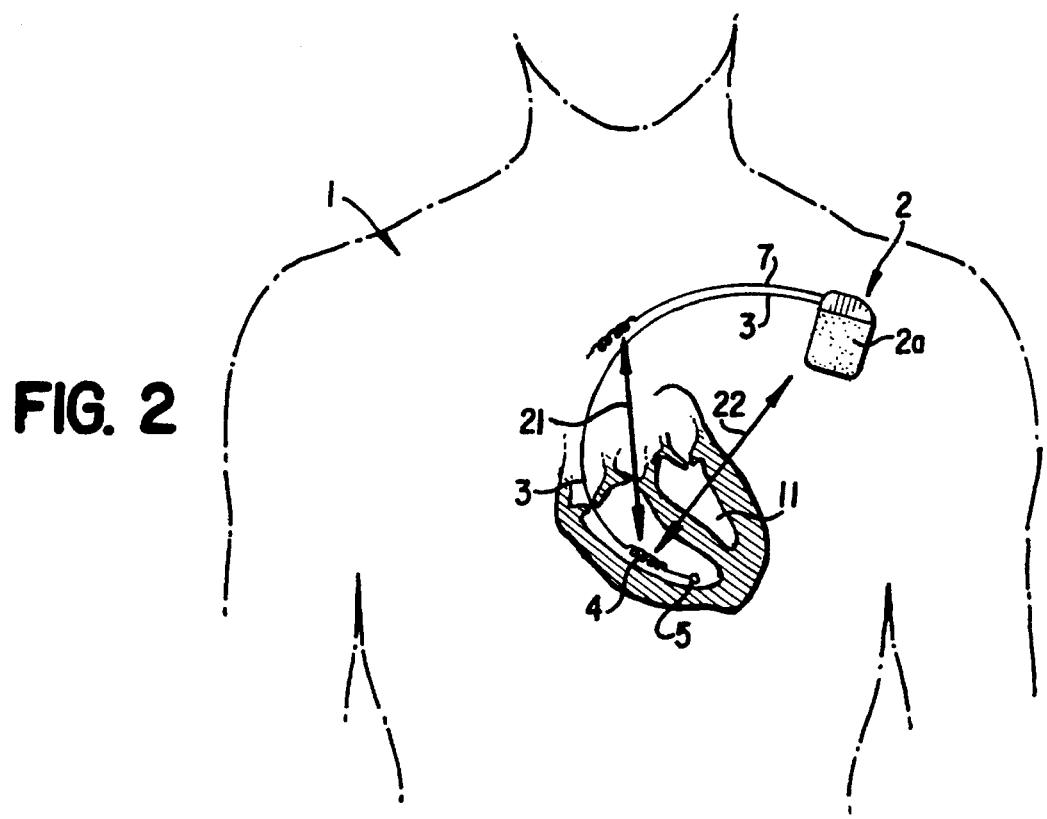
FIG. 2 is a view similar to that of FIG. 1, illustrating the electric field vectors produced between the electrodes and the stimulus generator case during operation of the device.

FIG. 2 schematically illustrates the main electric field vector 21 produced by a shock waveform delivered through the transvenous lead 3 and 7 with associated electrode coils 4 and 8, respectively, in the right ventricle and superior vena cava as was described with respect to FIG. 1. Previous research has demonstrated that the metal case of the defibrillator stimulus generator 2a may also be used as an anode or cathode relative to electrode coil 4 in the right ventricle to defibrillate the heart. With such an arrangement, a vector 22 is created from an electric field concentration which passes more directly through the center of the heart, including a larger portion of the mass of left ventricle 11.

We have found as a result of our studies, that application of a defibrillation pulse between an electrode coil 4 located in the right ventricle and the metal case 12 of the stimulus generator located in the retropectoral position, decreases the energy required for defibrillation by 30% to 50% with the electric field that creates vector 22, when compared to the electric field that creates vector 21. This finding has been confirmed and published by others. For example, see the article published by G. H. Bardy, "A simplified single lead unipolar transvenous cardioversion/defibrillation system" in *Circulation* 1993, 88:543–547.

Figure 3:
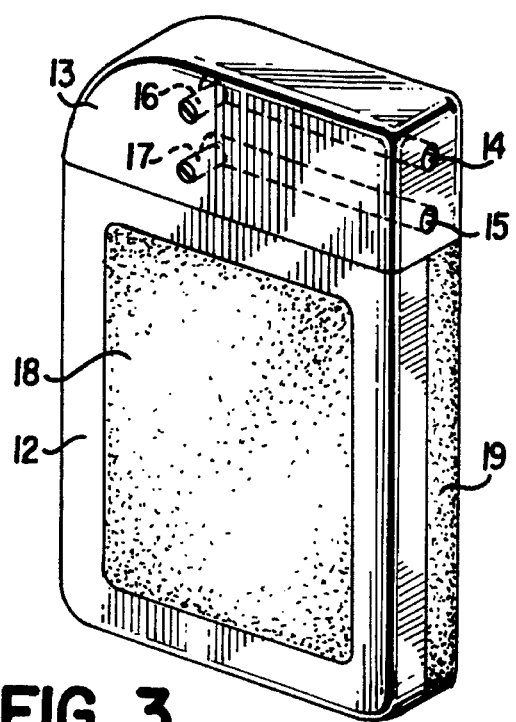
FIG. 3 is a perspective view from the front side of the stimulus generator case including the header for the lead connections, showing the preferred configuration of the electrical insulation coating on the case.

According to a presently preferred embodiment of our invention, a considerably reduced defibrillation threshold (DFT) is obtained by means shown in FIG. 3. The Figure illustrates a perspective view of the defibrillator stimulus generator case 12 from the front side which, when the generator is implanted, faces the patient's internal organs, especially the heart. A biocompatible, conforming, electrically non-conductive coating 18 is applied to the exterior surface of the front side of case 12 to extend over its entire central region while leaving exposed an outer margin at the boundary of that side. This outer margin or boundary edge region of the side of the case in question is preferably not more than about 1.0 centimeter in width. A suitable biocompatible, compliant, electrically non-conductive coating 18 for this purpose is parylene. However, other materials possessing such characteristics may alternatively be employed.

If the stimulus generator case 12 is implanted in a retropectoral position, the front side of the case with its electrically insulated portion as described above will face the patient fibs. If implanted instead in a subcutaneous position, the front side faces the pectoral muscle. In any event, the side covered with the insulative coating but exposing the conductive portion of the case adjacent the edge at that side should always face toward the patient's heart. Preferably, the stimulus generator is implanted in the pectoral region at the patient's left side, to enhance the electrical field through the heart which is developed when the shocks are delivered by the stimulus generator.

Metal case 12 has a conventional header 13 of molded epoxy resin mounted on it which includes receptacles 14 and 15 for electrical connection of the transvenous leads to the appropriate portions of the electrical circuitry of the stimulus generator. Set screws 16 and 17 are provided to retain the leads in place after insertion and electrical check has verified good electrical contact.

Figure 4:
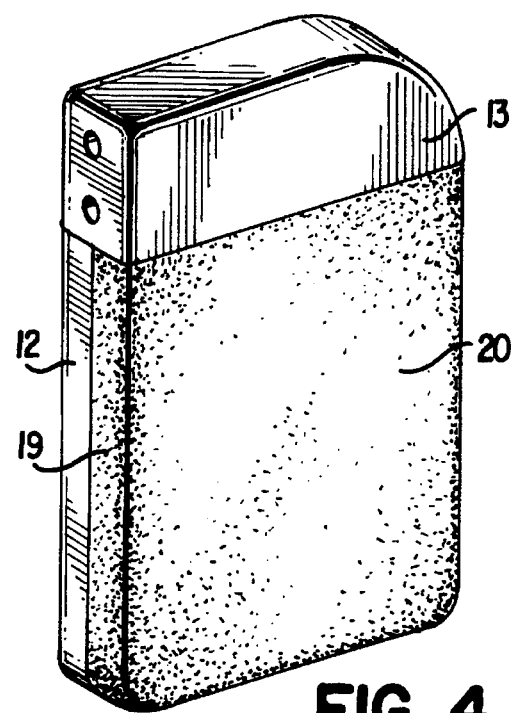
FIG. 4 is a perspective view of the opposite side of the stimulus generator case relative to the view illustrated in FIG. 3, showing an embodiment of the configuration of the electrical insulation coating on that side of the case.

FIG. 4 shows the opposite side of the stimulus generator case 12, intended to be positioned adjacent the skin of the patient after the generator is implanted. In the presently preferred embodiment, that side and approximately the adjacent one-half of the end wall 19 of the case are entirely covered with a coating layer 20 of the same coating material as was used for coating layer 18. As a result of the overall coating configuration, the only exposed conductive portion of the metal case is an outer ting structure at the boundary of the front side and extending along one-half of the end wall. Preferably, the conductive portion of the end wall is a band having a width of from 0.5 to 1.0 centimeter.

The provision of this outer ting portion of case 12 as the entire electrically conductive region is in contrast to the prior art technique in which the entire defibrillator case is exposed as an electrode for defibrillation purposes. We have found that by using only this outer conductive ting electrode in the left pectoral region together with a defibrillation electrode coil in the right ventricle, the electric field concentration produces a many-fold increase in field strength over the prior art technique.

Figure 5:
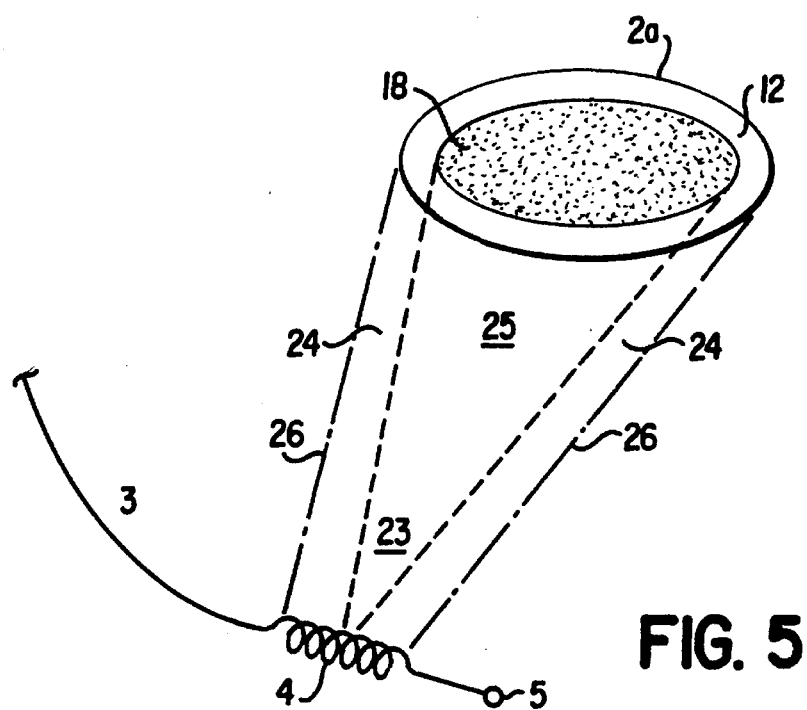
FIG. 5 is a schematic diagram illustrating the field strength and concentration between portions of the implanted stimulus generator case and an endocardial electrode, employing the preferred embodiment of the insulatively coated case.

The field produced by this configuration is illustrated schematically in FIG. 5. If non-conductive coating 18 were not present on the front side of case 12 so that the entire case was electrically conductive, the electric field 23 between the right ventricular electrode coil 4 and case 12 resulting from application of an electrical shock waveform across the two would be quite homogeneous throughout and have an approximate boundary at heavily dashed lines 26. The field strength is equally distributed because of the conductivity of the entire case or side.

In contrast, with the non-conductive coating layer configuration according to the invention, as shown in FIGS. 3 and 4, and the exposed portion of the case serving as either anode or cathode for defibrillation shocks, the current and voltage developed by the electric field attributable to delivery of the shock waveform are concentrated in a much smaller outer ting or channel area 24 (FIG. 5). The boundary of the channel is depicted by dotted lines and dashed lines in the Figure. The central portion 25 within this channel- or ring-like field is of considerably lower field strength than in the channel itself. However, we have found that this lower field strength at the center is not critical because it is still sufficient to defibrillate the tissue in the portion of the heart within that central region 25.

The substantially higher field strength in channel 24 produces a voltage drop to the outer portion of the heart which is more favorable for achieving a minimum voltage gradient. The result is a substantially lower energy requirement for generating the critical field to defibrillate even the most remote part of the heart, and thus, a correspondingly lower DFT. The lower DFT, compared to conventional defibrillation techniques, allows the size of the batteries and capacitors of the stimulus generator to be markedly reduced, to thereby reduce the overall size of the generator itself.

Measurements conducted by us in our research indicate a 30% to 40% reduction in DFT (a reduction from about 18.8 joules to about 11.1 joules, for example, in one test case) is attainable using the single coil configuration of the invention versus the use of two transvenous lead electrode coils according to the prior art technology. A further substantial improvement of 20% to 30% reduction in DFT ((a reduction from about 12.5 joules to about 9.7 joules, for example, in another test case) is achieved using a case having shaped or patterned zones of conductivity and nonconductivity according to the invention, compared to the use of the overall case as an electrode.

In addition to the advantage of the non-conductive coating on the back side of the stimulus generator case in helping to force the current in a way that increases the field strength in the most critical region, it reduces stimulation of the pectoral muscle and consequent tendency to twitch during unipolar pacing between case 12 and pacing tip 5. Also, the back side insulating coating tends to decrease muscle noise for sensing in a unipolar mode between either the pacing tip 5 and the case 12 or the coil 4 and the case 12, and to improve sensing in a differential manner between electrodes 4 and 12 and 5 and 12, respectively, with a differential built-up between the two sensing vectors. The latter increases both the sensitivity and the specificity of tachycardia recognition.

The coating layer may be applied to the defibrillator stimulus generator case in an entirely similar manner to that conventionally used for coating cardiac pacemaker pulse generators, except for the configuration of the coating that allows the outer ring edge of the case to be exposed conductively in the present invention.

It will be appreciated from the foregoing description and results that this coating configuration in the central region of the front side of the stimulus generator case provides a substantial improvement in the effectiveness of the shock and in reduction of DFT, which allows the use of cosmetically desirable, smaller-sized implantable defibrillators without loss of effectiveness (and even enhanced effectiveness) relative to the considerably larger-sized defibrillators prevalent in the prior art.

Although a best mode of practicing the invention has been described in this specification, it will be apparent to those skilled in the field to which the invention relates that variations and modifications may be made without departing from the true spirit and scope of the invention. Accordingly, it is intended that the scope of the invention shall be limited only by the appended claims and the principles and rules of applicable law.

What is claimed is:

1. An automatic defibrillator adapted to be implanted in the body of a patient, comprising stimulus generator means for sensing fibrillation of the patient's heart and responsive thereto for delivering defibrillation energy to the patient's heart via a defibrillation electrode adapted to be positioned in the heart, an electrically conductive case housing said stimulus generator means, and a conforming biocompatible electrically insulating layer coating a central region at a side of the case which is to face inwardly of the patient's body when the stimulus generator means is implanted, to leave at least a portion of the edge bounding said side uninsulated and thereby produce a predetermined electric field concentration between said defibrillation electrode and the uninsulated portion of the boundary edge of said side when the case is used as an electrode for defibrillation.

2. The defibrillator of claim 1, in which the entire boundary edge of said side is left uninsulated.

3. The defibrillator of claim 2, in which said uninsulated boundary edge is up to approximately one centimeter wide.

4. The defibrillator of claim 2, in which an end wall of said case between said side and an opposite side of the case which is to face outwardly of the patient's body when the stimulus generator means is implanted is partially coated with said insulating layer to expose an uninsulated surface ring of said end wall adjacent said boundary edge.

5. The defibrillator of claim 4, in which said opposite side of the case is coated at least substantially entirely with said insulating layer.

6. The defibrillator of claim 1, further including a ventricular lead having said defibrillation electrode adapted to be positioned in the right ventricle of the heart.

7. The defibrillator of claim 1, further including an atrial lead having said defibrillation electrode adapted to be positioned in the right atrium of the heart.

8. A method of defibrillating a patient's heart with an automatic implanted defibrillator, comprising the steps of sensing fibrillation of the patient's heart and responding thereto by delivering defibrillation energy to the patient's heart from a stimulus generator of the defibrillator via a defibrillation electrode in the heart, using the electrically conductive case that houses the stimulus generator as a second electrode for defibrillation, and concentrating an electric field attributable to the delivery of defibrillation energy between the defibrillation electrode and the second electrode over a predetermined portion constituting less than all of a side of the case facing inwardly of the patient's body.

9. The method of claim 8, in which the concentrating of the electric field is achieved by using a case with an electrically insulating coating on a predetermined portion less than all of said side.

10. The method of claim 9, in which the case with said insulating coating on said side is provided by coating a central portion of said side with an insulating layer to leave at least a portion of the edge bounding said side uninsulated.

11. The method of claim 10, in which the coating step is performed by coating all of said side except the entire boundary edge thereof with said insulating layer.

12. The method of claim 11, in which the coating step is performed to leave an uninsulated boundary edge having a width of up to approximately one centimeter.

13. The method of claim 11, in which said coating step is performed to include partially coating an end wall of said case between said side and an opposite side of the case that faces outwardly of the patient's body when the case is implanted, with said insulating layer to expose an uninsulated surface ring of said end wall adjacent to said entire boundary edge.

14. The method of claim 13, in which said coating step is performed to include coating said opposite side of the case at least substantially entirely with said insulating layer.

15. The method of claim 8, including the steps of implanting said stimulus generator in the left pectoral region of the patient's chest, and positioning said defibrillation electrode in the right ventricle of the patient's heart.

16. The method of claim 8, including the steps of implanting said stimulus generator in the left pectoral region of the patient's chest, and positioning said defibrillation electrode in the right atrium of the patient's heart.

17. An automatic, body-implantable defibrillator device comprising an electrical waveform generator for detecting fibrillation of atrial or ventricular chambers of a patient's heart and for response thereto by generating defibrillation energy to be delivered to the fibrillating chambers, and an electrically conducting case with a pair of side walls separated by an end wall to form a sealed enclosure for said generator, said case having an electrically insulating external surface pattern to render at least a substantial part of an exposed surface of each of the side walls insulated and an exposed surface of the end wall uninsulated in a surface ring configuration.

18. The device of claim 17, in which the exposed surface of said end wall is uninsulated in said surface ring configuration only adjacent the periphery of one of said side walls and the remainder of the exposed surface of said end wall is insulated, and the edge of said one of said side walls at said periphery thereof is also uninsulated and joins said uninsulated surface ring configuration of the end wall.

19. A method of establishing an electric field pattern conducive to defibrillating the atrial or ventricular chambers of a patient's heart with relatively low energy levels, said method comprising the steps of positioning a pair of defibrillation electrodes with one of said pair on a transvenous lead and located in a chamber to be defibrillated at the right side of the heart, and with the other of said electrodes being an electrically conducting housing of a defibrillation waveform generator implanted in the left pectoral region of the patient with a pattern of insulating material on the surface of said housing exposed to said transvenous lead electrode so that when a defibrillation waveform is delivered across said pair of electrodes the electric field produced therebetween is concentrated in a ring-like pattern at the periphery of said housing relative to said transvenous lead electrode.

20. A method of preparing the electrically conducting housing of an implantable defibrillation waveform generator for use as one defibrillation electrode for interaction with another defibrillation electrode located on a transvenous lead to be introduced into a chamber in the right side of a heart, said method comprising applying a layer of electrically insulating biocompatible material onto an external surface of said housing and conforming thereto in a pattern wherein at least a substantial part of an exposed surface of each of a pair of side walls of said housing is insulated and an exposed surface of an end wall of said housing separating said side walls to form a sealed enclosure is left uninsulated as a conducting surface ring configuration.

21. The method of claim 20, further comprising leaving the exposed surface of said end wall uninsulated in said conducting surface ring configuration only adjacent the periphery of one of said side walls and the remainder of the exposed surface of said end wall insulated, and leaving the edge of said one of said side walls at said periphery thereof also uninsulated to join said conducting surface ring configuration of the end wall.

\* \* \* \* \*